US006790441B1

(12) United States Patent
Cameron et al.

(10) Patent No.: US 6,790,441 B1
(45) Date of Patent: Sep. 14, 2004

(54) SERTOLI CELLS AS BIOCHAMBERS

(75) Inventors: Don F. Cameron, Lutz, FL (US); Paul R. Sanberg, Spring Hill, FL (US); Samuel Saporta, Tampa, FL (US); Joelle J. Hushen, Lithia, FL (US)

(73) Assignee: University of South Florida, Tampa, FL (US)

( * ) Notice: Subject to any disclaimer, the term of this patent is extended or adjusted under 35 U.S.C. 154(b) by 0 days.

(21) Appl. No.: 09/593,629

(22) Filed: Jun. 13, 2000

(51) Int. Cl.$^7$ .......................... A01N 65/00; C12N 5/02; C12N 5/06; C12N 5/00

(52) U.S. Cl. ...................... 424/93.1; 435/325; 435/347; 435/373; 435/382; 435/383

(58) Field of Search ............................... 424/93.1, 93.7, 424/559; 435/325, 347, 373, 382, 383

(56) References Cited

U.S. PATENT DOCUMENTS

| | | | |
|---|---|---|---|
| 5,702,700 A | | 12/1997 | Sanberg et al. |
| 5,725,854 A | | 3/1998 | Selawry |
| 5,759,534 A | | 6/1998 | Selawry |
| 5,827,736 A | | 10/1998 | Heller et al. |
| 5,830,460 A | | 11/1998 | Sanberg et al. |
| 5,843,430 A | * | 12/1998 | Selawry ..................... 424/93.7 |
| 5,849,285 A | | 12/1998 | Selawry |
| 5,942,437 A | * | 8/1999 | Sanberg et al. ............. 435/374 |
| 5,958,404 A | | 9/1999 | Selawry |
| 6,001,643 A | * | 12/1999 | Spaulding ................ 435/298.2 |
| 6,036,951 A | | 3/2000 | Sanberg et al. |
| 6,037,175 A | | 3/2000 | Cameron et al. |

FOREIGN PATENT DOCUMENTS

| | | |
|---|---|---|
| WO | WO 96/28174 A1 | 9/1996 |
| WO | WO 96/33264 A1 | 10/1996 |
| WO | WO 97/33470 A1 | 9/1997 |
| WO | WO 01/66698 A1 | 9/2001 |

OTHER PUBLICATIONS

Moira A. L. Maley et al. Extracellular Matrix. Growth Factors. Genetics Their influence on Cell Proliferation and Myotube Formation in Primary Cultures of Adult Mouse Skeletal Muscle. Experimental Cell Research. 219. pp 169–179 ATCC. pp. 1–7.*
Willing et al Sertoli cell transplants their use in the treatment of neurodegenrative disease Nov. 1998 pp 474–477.*
Korbutt Testicular sertoli cells exert both protective and destructive effects on syngeneic islet grafts in non–obese diabetic mice 2000 pp 474–480.*
Korbutt et al, Diabetologia 2000 Apr;43:474–80.*
Hadley et al, J Cell Biol 1985;101:1511–22.*
Van der Wee et al, Exp. Cell Res 1999;252:175–85.*
Hadley et al. J Cell Biol 1985:101:1511–22.*
van der Wee et al. Exp Cell Res 1999:252:175–85.*

Byers S et al "Sertoli Cell Junctions and the Seminiferous Epithelium Barrier", pp 431–446, in *The Sertoli Cell*, L D Russell and M.D. Griswold. Eds. Cache River Press, 1993.
Cameron, D F et al "Longterm Microgravity Coculture of Sertoli Cells and Islets Enhances Insulin Secretion"*Endocrin. Proc.*, Jun. 15, 1999. P2–230, abstract.
Cameron, D.F. et al "Formation of Sertoli Cell–Enriched Tissue Constructs Utilizing Simulated Microgravity Technology" *Annals New York Acad. Sci.*, Nov. 2001. 944. 420–428.
Cameron, D F et al "Formation of Insulin–Secreting, Sertoli–Enriched Tissue Constructs by Microgravity Coculture of Isolated Pig Islets and Rat Sertoli Cells" *In Vitro Cell Dev Biol.–Animal*, Sep. 2001, 37. 490–498.
Clermont, Y., "Introduction to the Sertoli Cell", pp. XXI–XXV, in *The Sertoli Cell*. L D Russell and M D Griswold Eds. Cache River Press, 1993.
De Cesaris P et al "Immunosuppressive Molecules Produced by Sertoli Cells Cultured in vitro Biological Effects on Lymphocytes" *Biochemical and Biophysical Res Comm.* Aug. 14, 1992, 186(3): 1639–1646.
Djakiew, D and M. Onoda Multichamber Cell Culture and Directional Secretion pp 181–194, in *The Sertoli Cell* L D Russell and M D Griswold. Eds. Cache River Press, 1993.
Free M J et al Respiratory Gas Tensions in Tissues and Fluids of the Male Rat Reproductive Tract *Biology of Reproduction*, 1976 14: 481–488.
Whitmore, W F et al "The Role of Germinal Epithelium and Spermatogenesis in the Privileged Survival of Intratesticular Grafts" *The J. Urology*, Oct. 1985, 134 782–786.
Wyatt, C R et al "Suppression of lymphocyte proliferation by proteins secreted by cultured Sertoli cells" *J Reproductive Immunology* 1988 14 27–40.
Alderson, D. et al (1987). The Isolation of Purified Human Islets of Langerhans. *Transplant Proc.* 19:916–917.
Alison E. et al (1998). Sertoli cell transplants: their use in the treatment of neurodegenerative disease. Mol. Med. Today, 4:471–477.
Bardin, C.W, et al (1988). The Sertoli Cell. In: *The Physiology of Reproduction*. Knobil, E. and J. Neil (eds). Raven Press, Ltd., New York. Pp 933–974.

(List continued on next page.)

Primary Examiner—Anne M. Wehbe
Assistant Examiner—Q. Janice Li
(74) Attorney, Agent, or Firm—Saliwanchik, Lloyd & Saliwanchik (57) ABSTRACT

According to the present invention, there is provided a biological chamber system having a biochamber defined by outer walls of Sertoli cells. Also provided is a transplantation facilitator including a biochamber. A method of making biochambers by co-culturing facilitator cells and therapeutic cells and then aggregating the facilitator celes is also provided. Also provided is a method of transplanting cells by incorporating transplant cells into a biochamber and transplanting the biochamber containing the transplant cells.

25 Claims, 6 Drawing Sheets

OTHER PUBLICATIONS

Barker, C.F. et al (1968). The Role of Afferent Lymphocytes in the Rejection of Skin Homografts. *J. Exp. Med.* 128:197–221.

Becker, J.L. et al (1993). Three–Dimensional Growth and Differentiation of Ovarian Tumor Cell Line in High Aspect Rotating–Wal Vessel: Morphologic and Embryologic Considerations. *J. Cellul. Biochem*, 51:283–289.

Bellgrau, D., et al (1995), A role for CD95 Ligand in Preventing Graft Rejection. *Nature*, 377:630–632.

Borlongan, C.V. et al (1996). Functional recovery in female hemiparkinsonian rats following transplantation of Sertoli cells. Proc. Am. Soc. Nuer. Transp.

Borlongan, C.V. et al (1997). Intracerebral transplantation of testis–derived Sertoli cells in female rats with 6 hydroxydopmine induced hemiparkinsonian promotes functional recovery. Exp. Neurol. 148:388–392.

Born, W. and H. Wekerle (1982). Leydig Cells Nonspecifically Suppress Lymphoproliferation in Vitro: Implications for the Testis as an Immunologically Privileged Site, *Am. J. Reprod, Immunol.* 2:291–295.

Born, W. et al (1981). Selective, Immunologically Nonspecific Adherence of Lymphoid Cells and Myeloid Cells to Leydig Cells. *Eur. J. Cell Biol.* 25:76–81.

Calafiore, R. et al (1990). A Method for the Massive Separation of Highly Purified, Adult Procine Islets of Langerhans. *Metabolism.* 39:175–181.

Cameron,D.F. et al (1990). Successful Islet/Abdominal Testis Transplantation Does Not Require Leydig Cells, *Transplantation.* 50:649–653.

Cameron, D.F. et al (1990). Sustained Hyperglycemia Results in Testicular Dysfunction and Reduced Fertility Potential in BBWOR Diabetic Rats. *J. Physiol.*, 259 (Endocrinol. Metab., 22); E881–E889.

Cameron, D.F. et al (1991). Hormonal Regulation of Spermatid Binding to Sertoli cells In Vitro, *J. Cell. Sci.*, 100:623–633.

Cameron, D,F. et al (1993). Testosterone Stimulates Spermatid Binding to Competent Sertoli cells In Vitro, *Endocrinol. J.* 1:61–65.

Cameron, D.F. et al (1996). Enhanced post–thaw viability of cryopreserved rat fetal brain cells by Sertoli cells by Sertoli cell Secretory products. Proc. Am. Soc. Neural. Transpl.

Cameron, D.F. et al (1997). Post–thaw viability and functionality cryopreserved rat fetal brain cells co–cultured with Sertoli cells. Cell Transplant, 6:185–189.

Cameron, D.F. et al (1998). Development of Sertoli cell binding competence in the peripubertal rat, J. Andrology, 19:573–579.

Cantrell, D.A. et al (1984). The Interleukin–2 T–Cell system: A New Cell Growth Model. *Science,* 224:1312–1316.

Chervonsky, A.V. et al (1997). The role of Fas in autoimmune diabetes. *Cell*, 89:17.

DeCesarts, A. et al (1992), Inhibition of Lymphocyte Activation by Sertoli Cell Immunosuppressive Factor(s), *Immunologia et Immunofarmacologia*, 12(2):86.

Edgington, S.M. (1992), New Horizons for Stem–Cell Bioreactors, *Bio/Technology* 10:1099–1106.

Evans M.G. et al (1990). Reversal of Diabetes in Dogs by Transplantation of Pure cryopreserved Islets. *Transplantation.* 50:202–206.

Fawcett, D.W. et al (1973). Comparative Observation on Intertubular Lymphatics and the Organization of the Interstitial Tissue of the Mammalian Testis. *Biol. Reprod.* 9:500–512.

Gainer, A.L. et al (1998). Improved survival of biolistically transfected mouse islet allografts expressing CTLA4–Ig or soluble Fas ligand. *Transplantation.* 66:194–9.

Gondos, B. et al (1993). Postnatal and Pubertal Development. In: *The Sertoli Cell*, 1993, Russell LD, Griswold MD (eds). Cache River Press, Clearwater, Florida, pp 493–508.

Goodwin, T.J. et al (1992). Morphologic Differentiation of Colon Carcinoma Cell Lines HT–29 and HT–29KM in Rotating Wall Vessels, *In Vitro Cell. Dev. Biol.* 28A:47–60.

Goodwin, T.J. et al (1993). Reduced Shear Stress: A Major Component in the Ability of Mammalian Tissues to Form Three–Dimensional Assemblies in Stimulated Microgravity. *J. Cellul. Biochem.* 51:301–311.

Goodwin, T.J. et al (1993). Rotating–Wall Vessel Coculture of Small Intestine as a Prelude to Tissue Modeling: Aspects of Stimulated Microgravity. *Proceed Experiment. Biol. Med.* 202:181–192.

Gray, D.W.R. et al (1984). A Method for the Isolation of Islets of Langerhans from the Human Pancreas. *Diabetes.* 33:1055–1061.

Green, C.J. et al (1978). Extensive Prolongation of Rabbit Kidney Allograft Survival after Short–Term Cyclosporin—A Treatment. *Lancet.* 1:182–1183.

Griswold MD. Actions of FSH on mammalian Sertoli cells. In: *The Sertoli Cell*, 1993. Russell LD, Griswold MD (eds). Cache River Press, Clearwater, Florida, pp 493–508.

Hadley, M. et al (1985). Extracellular matrix regulates Sertoli cell differentiation, testis cord formation and germ cell development in vitro. *J. Cell Biol.* 101:1511–22.

Head, J. et al (1983). Immune Privilege in the Testis. I. Basic Parameters of Allograft Survival. *Transplantation,* 36:423–431.

Head, J., et al (1983), Reconsideration of the Lymphatic Drainage of the Rat Testis. *Transplantation:* 35:91–95.

Hedger, M.P. (1989), The Testis as an "Immunologically Suppressed" Tissue? *Reprod. Fertil. Dev.* 1:75–81.

Hess, A.D. (1985), Effect of Interleukin 2 on the Immunosuppressive Action of Cyclosporine. *Transplantation,* 39:62–68.

Homan, W.P. et al. (1980), Studies on the Immunosuppressive Properties of cyclosporin A in Rats Receiving renal Allografts. *Transplantation*, 29:361–366.

Horaguchi, A. and R.C. Merrell (1981), Preparation of Vible Islet Cells from Dogs by a New Method. *Diabetes.*, 30:455–458.

Kang, S–M. et al (1997), Fas ligand expression in islets of Langerhans does not confer immune privilege and instead targets them for rapid destruction. *Nature Med.* 3:738.

Kaufman, D.B. et al (1990), Functional Outcome as Influenced by Islet Number and Implantation Site. *Transplantation*, 50:385–391.

Kneteman, N.M. et al (1986), Isolation and Cryopreservation of Human Pancreatic Islets. *Transplant. Proc.* 18:182–185.

Kneteman, N.M. et al (1990). Prolonged Function of Canine Fragments Autotransplanted to the Spleen by Venous Reflux. *Transplantation*, 49:679–681.

Kuhn F., et al (1985), Morphological Investigations in Human Islets of Langerhans Isolated by the Velcro Technique, *Biomed. Biochem. Acta.* 44:149–153.

Lau, H, et al (1996), Prevention of islet allograft rejection with engineered myoblasts expressing FasL in mice. *Science*, 273:109.

Leapman, S.B., et al (1981), Differential Effects of Cyclosporine A on Lymphocyte Subpopulations. *Transplant Proc.* 13:405–409.

London, N.J.M. et al (1990), A Simple Method for the Release of Islets by Controlled Digestion of the Human Pancreas. *Transplantation* 49: 1109–1113.

Martin, D.C. (1982), Malignancy in the Cryptorchid Testis. *Urol. Clinics N. Amer.* 9:371–376.

Muruve, D. et al (1997). Adenovirus–mediated expression of Fas ligand indices hepatic apoptosis after systemic administration and apoptosis of ex vivo–infected pancreatic islet allografts and isografts. *Human Gene Ther.* 8:955.

Naji, A. et al (1981), Prevention of Diabetes in Rats by Bone Marrow Transplantation. *Ann. Surg.* 194:328–338.

Ogasawara, J. et al (1993), Lethal effect of the anti–Fas antibody in mice. *Nature*, 364:806.

Othberg, A.I. et al (1998), Preparation of cell suspension for co–transplantation: methodological considerations, Neurosci let., 247:111–114.

Othberg, A.I. et al (1998). Trophic effect of porcine Sertoli cells on rat and human ventral mesencephalic cells and hNT neurons in vitro. *Cell Transplant.*, 7:157–164.

Prowse, S J. et al (1986), Islet Allografts are Destroyed by Disease Occurence in the Spontaneously Diabetic BB *Rat, Diabetes*, 35:110–118.

Ricordi, C. et al (1989), Automated Islet Isolation from Human Pancreas. *Diabetes.* 38 (Suppl. 1):140–142.

Ricordi, C., et al (1990). Isolation of the Ilusive Pig Islet, *Surgery*, 107:688–694.

Sanberg, P.R. et al (1966), New horizons in xenograft cross–species transplantation for neurodenegerative disease. Proc. Internat. Behav. Neurosci. Soc.

Sanberg, P.R. et al (1995), The effects of Sertoli cell co–transplantation with chromaffin cells in the rat model of Parkinson's disease. Nature's Letters (In review).

Sanberg, P.R. et al (1996). Testis–derived Sertoli cells survive and provide localized immunoprotection for xenografts in rat brain. Nature Biotechnol. 14:1692–5.

Sanberg, P.R. et al (1996). Transplantation of testis–derived Sertoli cells into the Mammalian brain. Third Internat. Cong. Cell Transpl. Soc.

Sanberg, P.R. et al (1997), Testis–derived cultured Sertoli cell as a natural FasL secreting cell for immunosuppressive cellular therapy, *Cell Transplant.*, 191–193.

Sanberg, P.R. et al (1997). Testis–derived Sertoli cells have a trophic effect on dopamine neurons and alleviate hemiparkinsonian in rats. *Nature Medicine*, 3:1129–1132.

Scharp, D.W. (1988), The Elusive Human Islet; Variables Involved in its Effective Recovery, In: VanSchilgaard R., Hardy M.A. eds, *Transplantation of the Endocrine Pancreas in Diabetes Mellitus*. Amsterdam Elsevier, p. 97.

Scharp, D.W. et al (1987). Low Temperature Culture of Human Islets Isolated by the Distention Method and Purified with Ficoll or Percoll Gradients. *Surgery*. 102:869–879.

Schwarz, R.P. et al (1992). Cell Culture for Three–Dimensional Modeling in Rotating–Wall Vessels: An Application of Stimulated Microgravity. *J. Tiss. Cult. Meth.* 14:51–58.

Selawry, H. et al (1993). Sertoli Cell–Enriched Fractions in Successful Islet Cell Transplantation. *Cell Transplantation* 2:123–129.

Selawry, H. et al (1993), Sertoli Cell–Enriched Fractions in Successful Islet Cell Transplantation. *Cell Transplantation*, 2:123–129.

Selawry, H., et al (1986). Effect of Cyclosporine on Islet Xenograft Survival in the BB/W Rat. *Transplantation.* 42:568–575.

Selawry, H., et al (1987), Extended Survival of the MHC–Compatible Islet Isografts in the Spontaneously Diabetic BB/W Rat. *Diabetes.* 36:1061–1070.

Selawry, H.., et al. Production of a Factor, or Factors, Suppressing II–2 Production and T cell Proliferation by Sertoli Cell–Enriched preparations. *Transplantation*, 52:846–850.

Selawry, H.P. et al (1989). Abdominal Intratesticular Islet–Xenograft Survival in Rat, *Diabetes.* 38:220–223.

Selawry, H.P. et al (1996). Sertoli Cell–induced Effects on Functional and Structural Characteristics of Isolated Neonatal Porcine Islets. *Cell Transplantation*, 5:517–24.

Selawry, H.R. et al (1985). Intratesticular Islet Allografts in the Spontaneously Diabetic BB/W Rat. *Diabetes.* 34:1019–1023.

Skinner, M.K. (1993). Secretion of Growth Factors and Other Regulatory Factors, In: *The Sertoli Cell*, 1993. Russell L.D, Griswold MD (eds). Cache River Press, Clearwater, Florida. pp 493–508.

Tanaka, M. et al (1997), Lethal effect of recombinant human Fas ligand in mice protreated with Propionibacterium acnes. *J.Immunol.* 158:2303.

Thompson, S.C. et al (1990). Preparation and Assessment of Tissue for Transplantation and its In Vivo Development in Athymic (Nude Mice). *Transplantation*, 49:571–581.

Warnock, G.L. et al (1988), Studies of the Isolation and Viability of Human Islets of Langerhans, *Translantation*, 45:957–963.

Warnock, G.L., et al (1989), Viable Purified Islets from Collagenase–Perfused Human Pancreas. *Diabetes.* 38 (Suppl.1):136–139.

Weringer, E.J. et al (1985). Immune Attack on Pancreatic Islet Transplants in the Spontaneously Diabetci, Biobreeding/Worcester (BB/W) Rat is not MHC Restricted. *J. Immunol.* 134:2383–2391.

Whitmore, W.F. et al (1978), Intratesticular Grafts: The Testis as an Exceptionally Immunologically Privileged Site, *Trans. Am. Assoc. Gen–Urinary Surg.* 70:76–80.

Wickelgren, L (1996), Muscling Transplants into Mice, *Science.* 273:33.

Williams, H.J.H., P. Barkham, and N.G.P. Slater (1978). Testicular Relapse in Acute Leukemia, *Lancet.* 2:1152–1156.

Willing, A.E. et al (1998). Sertoli transplants to treat neurodegenerative disease. Mol. Med. Today, 4:471–477.

Willing, A,E. et al (1999). Sertoli cells decrease microglia response increase engraftment of human hNT neurons in the hemiparkinsonial rat straitum. *Brain Res. Bul.*, 48:441–444.

Willing, A.E. et al (1999). Sertoli cells enhance the survival of co–transplanted dopamine neurons. *Brain Research*, 822:246–250.

Yagita, H. et al (1996). CD95 ligand in graft rejection, *Nature*, 379–682.

* cited by examiner

SERTOLI CELLS AS BIOCHAMBERS

GRANT INFORMATION

Supported in part by NASA Grant NAG8-1381.

BACKGROUND OF THE INVENTION

1. TECHNICAL FIELD

The present inventions relates to methods of transplanting cells. More specifically, the present invention relates to methods of transplanting cells to create a localized immunosuppressive effect in the tissue receiving the transplanted cells.

2. BACKGROUND ART

The central nervous system (CNS) has poor regenerative capacity which is exemplified in a number of neurodegenerative disorders. An example of such a disorder is Parkinson's disease. The prefened pharmacotherapy for Parkinson's disease is the. administration of L-dopa which slows the progression of this disease in some humans. However, the neuropathological damage and the consequent behavioral deficits is not reversed by this treatment protocol.

Laboratory and clinical studies have shown that the transplantation of cells into the CNS is a potentially significant alternative therapeutic modality for neurodegenetative disorders such as Parkinson's disease (Wictorin et al., 1990; Lindvall et al, 1990; Sanberg et al., 1994; Bjorlund and Stenevi, 1985; Freeman et al, 1994). In some cases, transplanted neural tissue can survive and form connections with the CNS of the recipient (i.e. the host). When successfully accepted by the host, the transplanted tissue (i.e. the graft) has been shown to ameliorate the behavioral deficits associated with the disorder (Wictorin et al, 1990). The obligatory step for the success of this kind of treatment is the prevention of graft rejection (i.e. graft acceptance).

Currently, fetal neural tissue is the primary graft source for neural transplantation (Lindvall et al., 1990; Bjorklund, 1992; Isacson et al., 1986; Sanberg et, al 1994). Other viabie graft sources inclcude adrenal chromaffin cells and various cell types that secrete nerve growth factors and trophic factors. The field of neural tissue transplantation as a productive treatment protocol for neurodegenerative disorders has received much attention resulting in its progression to clinical trials. Preliminary results and clinical observations are promising although the graft rejection phenomenon remains problematic.

Transplantation is also a valuable therapy for other diseases, such as insulin dependent diabetes mellitus. Insulin dependent diabetes mellitus is a major health problem. Current forms of therapy are not efficient and do not necessarily lead to a prevention of diabetic complications such as renal failure or blindness. A desirable treatment alternative is to provide the diabetic with an endogenous source of insulin, transplanting either the whole pancreas or the endocrine component of the pancreas (i.e. islets of Langerhans) into the diabetic recipient. Although, whole pancreas transplantation is successfully achieved with at least 60% of the grafts still functioning after transplantation for one year, a major weakness of this approach is the need for continuous immunosuppfessicn with powerful and toxic immunosuppressant drugs.

The transplantation of the isolated islets containing the insulin secreting $\beta$-cells has received much attention in both animal models of diabetes (1–7) and in humans (8–16). However, islet transplantation to a variety of organ sites has met with little success as a viable treatment for diabetes. For example, islet transplantation of major histocompatibility complex (MHC) In the BB/W rat with spontaneous diabetes mellitus of autoimmune etiology results in destroyed islets within a few days by a recurrence of the autoimmune disease (17). Likewise, destruction of grafted cells in the diabeiic BB/W rat occurs in grafted islets of MHC-incompatibie donors (18, 19). In the course of finding a suitable organ or tissue site for islet transplantation, it was discovered that the relocated abdominal testis, in particular, provides an extraordinary safe environment for extended survival of islet grafts and some relief of the diabetic complications (20–22).

The testis has long been considered to be an immunologically privileged site (23–26) although the precise mechanism(s) by which it protects (suppresses) graft rejection has not been clearly defined. Isolated islets of MHC-compatible donors have been shown to survive for extended periods of time in the non-imminosuppressed BB/W rat if implanted in the rat's testis which is then placed into the host's abdominal cavity (20–22,27). Although the maintenance of functional islets allografts is significant, a more difficult task and far more potentially significant accomplishment, in terms of clinical applicability, is the induction of normoglycemia in diabetic animals by the implantation of cross-species islet xenografts.

Selawry and co-workers demonstrated the feasibility of such a procedure by successfully implanting incubated hamster islets into the BB/W rat abdominal testes (22,27,28). As a result of the abdominal testis/islet implant, the diabetic animals in these studies became normoglycemic. Long-term survival of the islet xenografts did not require prolonged immunosuppression to prevent rejection and to maintain normal sugar levels. In all cases implant viability required the protective milieu of the abdominal testis. It now appears that the donor origin of these isolated islets does not seem to influence their long-term survival. Islet cells grafted against major histocompatibility barriers (21), islet xenografts (27) and islets of MHC-compatible donors grafted into the testes of the diabetic BB/W rats functioned indefinitely in the recipient rendering the once diabetic animal normoglycemic.

The major weakness of this type of islet transplantation protocol is associated with the use of such an unconventional organ site. One major concern is the possibility of malignant transformation of germ cells at the higher core body temperature (29). More importantly, it would not be possible to use this transplantation protocol for the treatment of female diabetics.

Histological examination of grafted abdominal testes has shown that the islet implants are always found within the interstitial compartment of the gonad, which consists of the endocrine cells of Leydig, macrophages, blood vessels, testicular interstitial fluid and extracellular macromolecules (31). Any of the secretory products of these cells are potentially capable of inhibiting the immune response. For instance, Born and Wekerie (32, 33) showed that active suppression of immune responses occurred by Leydig cells in vitro. These investigators speculated that the Leydig cells might prevent lymphocyte proliferative responses by creating an "immunologically neutral zone" around the seminiferous tubules and thus decreasing the danger of T-cell infiltration in to the intratubular spaces. It was shown by Williams (34) that leukemic cells accumulate in the interstitial compartment where they are apparently protected against destruction by the host's immune defenses.

Figure 1A:
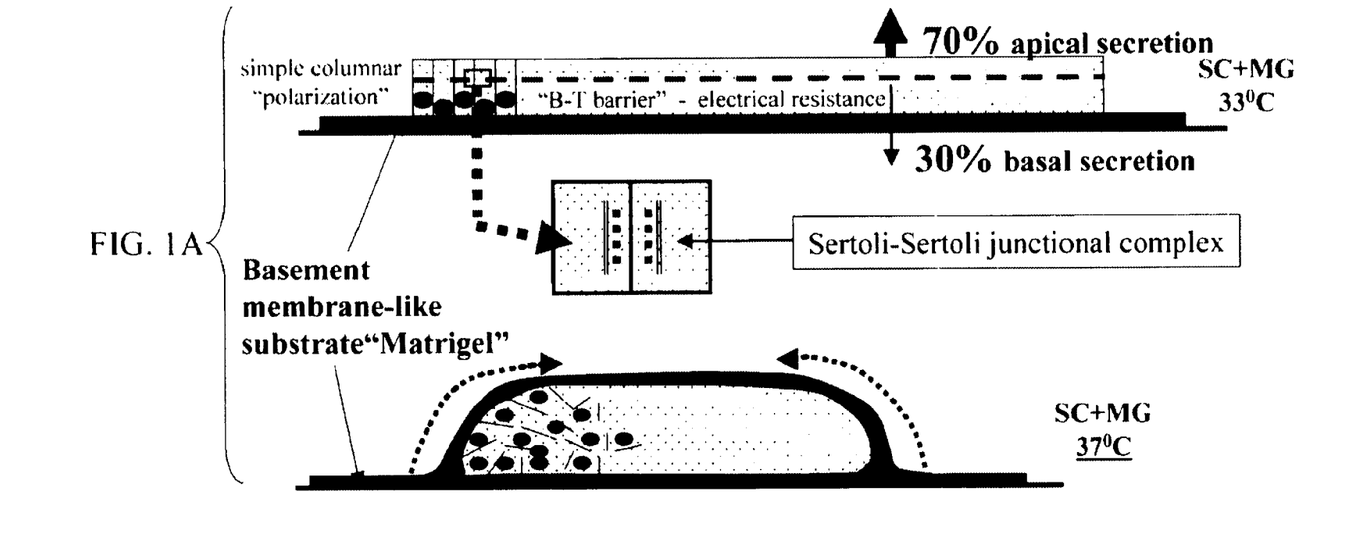
FIGS. 1A and 1B are diagrams showing the information of a biochamber on a substrate.
Figure 1B:
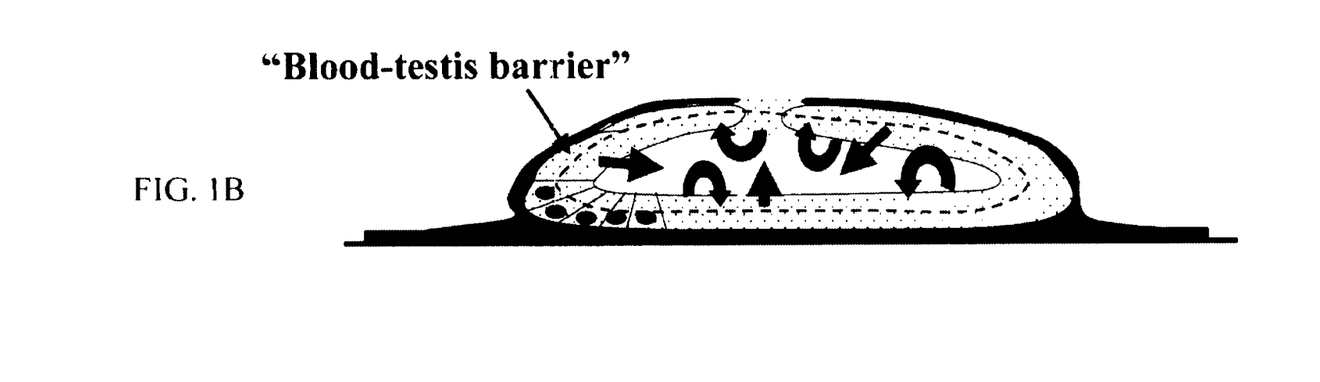

The "zone of protection" theory of Born and Wekerle (32) is attractive but it is not likely that this major component of the testicular interstitium, i.e. Leydig cells, is responsible for the synthesis of some protective (immunosuppressant) factor. Treatment of rats with ethane dimethanesulphonate (EDS), which selectively destroys the Leydig cell completely, including steroidogenesis and all other functions, had no adverse effects on the survival of intratesticular islet allografts (30). It is not probable that germ cells were involvedeither, since these cells are readily depleted in the abdominal testis. By eliminatin of these coils, Cameron and Sewiary concluded that the Sertoli cell was the most probable testicular cell type providing the testis with its unique immunologically privileged environment and that this cell was most likely responsible for the unexplained absence of islet rejection in abdominal testes (30). Based on these findings, Selawry and Cameron (35) attempted to create a similar immunologically privileged site outside of the testis utilizing Serioli cells as an immunosuppressant agent. To this end, isolated Sertoli cells were transplanted with isolated islets under the kidney capsule in female diabetic rats (see FIG. 1). Results from this study showed this novel transplantation protocol resulted in normoglycemia and that long-term islet allograft survival was achieved in a traditionally immunologically hostile site. We concluded that the Sertoli cell, independent of the testicular milieu, secreted an immunosuppressant factor(s) which was neither androgenic nor inhibitory to ovulation since 6 of the 7 mated recipients became pregnant, carried a pregnancy to term and nursed the pups successfully (35).

Figure 2A:
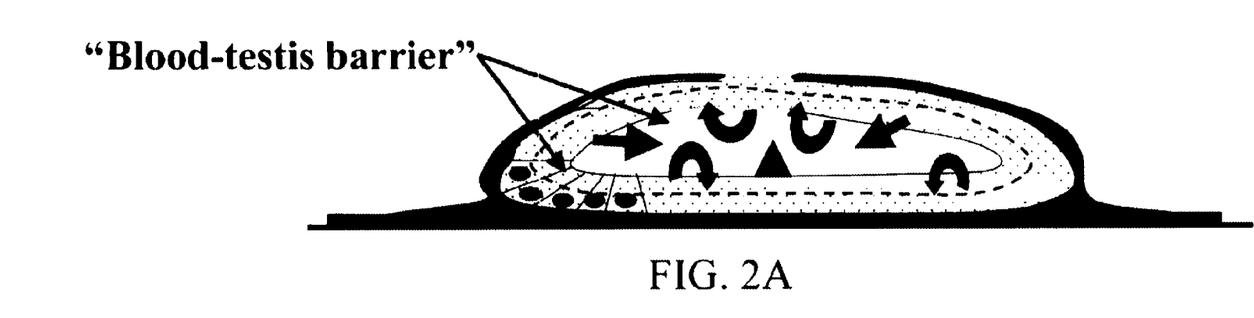
FIGS. 2A and 2B are diagrams comparing the differences between the conventional culture and a microgravity co-culture.
Figure 2B:
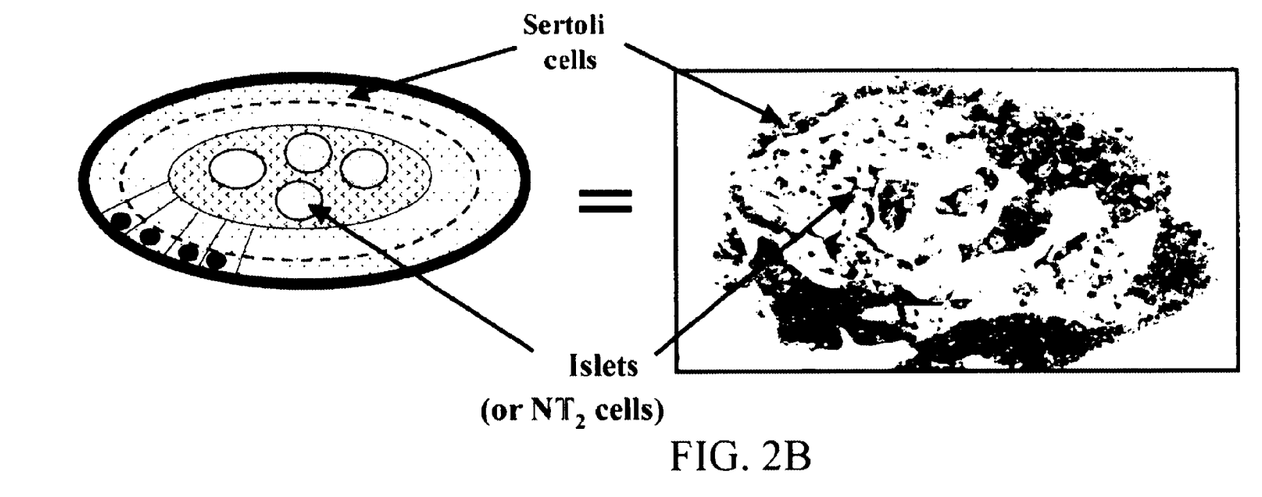
Figure 3:
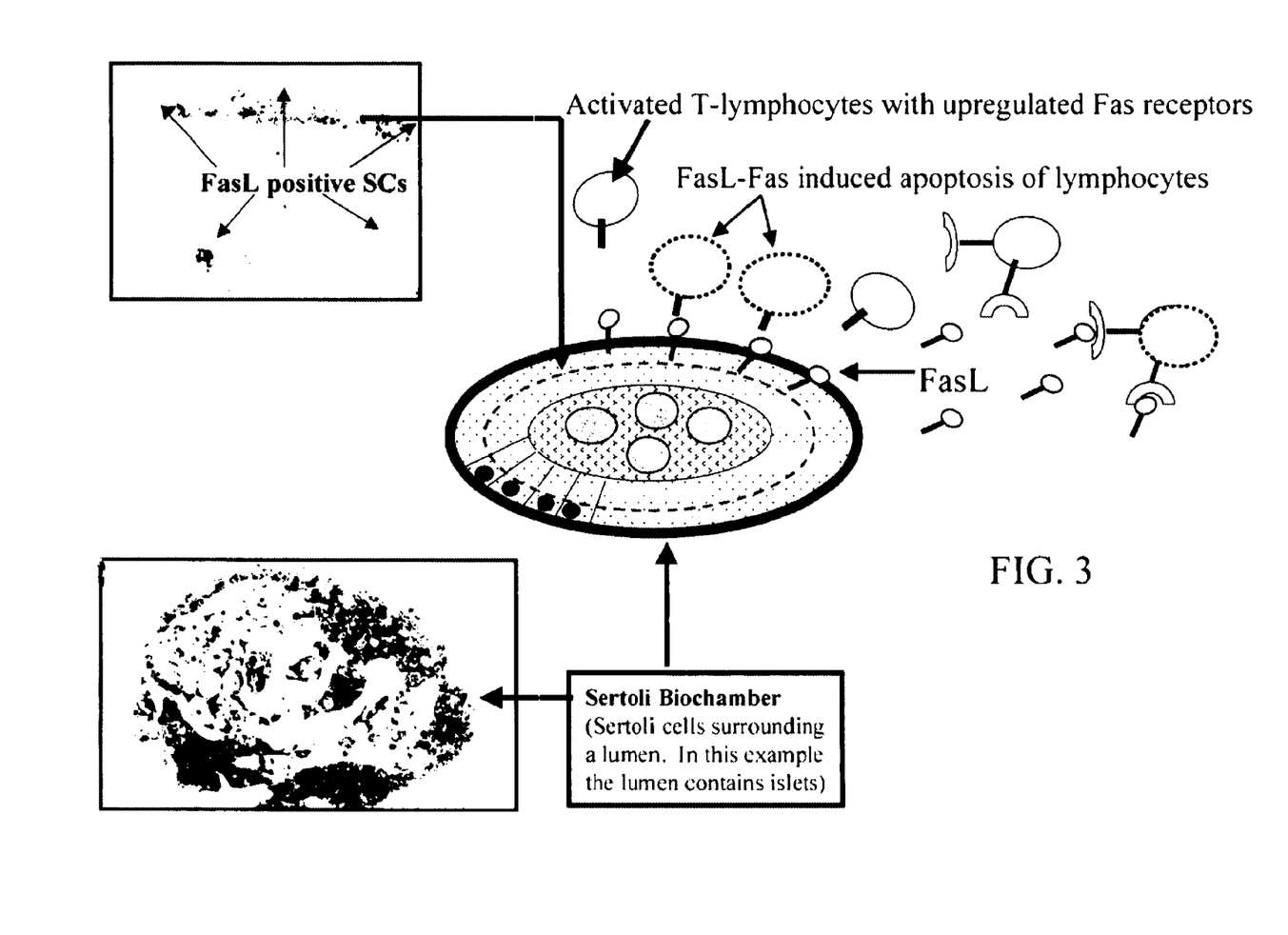
FIG. 3 is a mechanism showing the way the Sertoli cells effect immuno-suppression at the graft site. Positive FasL, immunostatining identifies Sertoli cells and suggest a mechanism by which they may effect immune suppression at the graft site. The expression of Fasl, by Sertoli cells induces apoptosis of the invading immune cells by binding to the upregulated Fas receptors on these activated T-lymphocytes. This results in the attrition of these immune cells at the graft site thereby down-regulating the immume responses—this by an already well-defined mechanism occuring naturally in the mammalian system.

For the long-term treatment of diabetes, it is clear that the presence of viable Sertoli cells is a prerequisite for long-term islet graph success and maintenance of long-term beta cell function. We do not yet clearly understand, however, the mechanism(s) which yield this observation. The likely explanation is that the Sertoli cells secret an immunosuppressant factor(s) which cooperates with exogenous immunosuppressants such as cyclosporine A to prevent a complete immune response and subsequently tissue rejection (35). Sertoli cells are active secretory cell types synthesizing many proteins. some of which promote growth and others which have immunosuppressive capabilities (36, 55). Initial studies to verify such a factor have been positive to date. The effects of Sertoli cell conditioned media on Con A-stimulated spleen lymphocyte proliferation showed that products secreted by Sertoli cells inhibit lymphocyte proliferation in a dose-dependent manner. The synthesis was temperature dependent, occurrinry predominantly at 37° C. and hormone dependent, requiring the presence of follicle stimulating hormone (FSH) in the Sertoli cell culture (see FIG. 2). We further examined the mechanism of inhibition of lymphocyte proliferation and showed that preconditioned Sertoli cell media inhibited the production of the lymphokine IL-2 in a dose-dependent manner (see FIG. 3A). Because the addition of exogenous IL-2 was not able to reverse this inhibition (see FIG. 3B), it appears likely that the preconditioned media inhibited both IL-2 production and T-lymphocyte responsiveness to IL-2 (38) in concurrence with similar finding by DeCesarts et al. (39) It is widely acknowledged that all proliferating T-cells express IL-2 receptors,. while resting cells do not, and that interaction of IL-2 with its receptor is an absolute requirement for the clonal expansion of activated T-cells (40). Because the prevention of IL-2 receptor interaction completely inhibits T-cell proliferation, we propose that both clonal expansion and viability of activated T-cells are suppressed by an immunosuppressive factor secreted by the Sertoli cells (35). In this fashion, the putative Sertoli cell derived immunosuppressant would appear to suppress the rejection by a mechanism similar to the action of cyclosporin A which also suppressed the production of IL-2 (41–44).

Although this hypothesis is appealing and with some research support of an indirect nature, it remains to be clearly unravelled. Recently, an additional and even more ppealing hypothesis has received consideration attention. Beligrau et al. (45*) in a letter to Nature showed that testis grafts that expressed Fas (CD95) ligand (FasL) survived indefinitely when transplanted under the kidney capsule, whereas testis grafts from gid mice (FasL deficient) were rejected when transplanted at the same site (45). A reverse transcriptase-polymerase chain reaction analysis demonstrated that Sertoli cells constitutively Pypress FasL mRNA. Additionally, they showed that isolated Sertoli cells derived from normal, but not the g/d mice survived indefinitely when transplanted under the kidney capsule. They concluded that the expression of functional FasL by Sertoli cells accounts for the immune-privilege nature of testis and suggested a mechanism by which Sertoli cells induce localized immune privilege to islets co-transplanted with Sertoli cells in an otherwise immune hostile site (i.e. subjacent the kidney capsule). They pointed out that FasL ligand-mediated immunosuppression would be expected to primarily target activated effector T cells rather than the activation steps that produce them, a mechanism by which Cyclosporin A produces immunosuppression. This would suggest that by targeting only activated T lymphocytes, grafted cell-associated FasL may provide a highly specific form of immunosuppression for ameliorating T-cell-dependent graft rejection. To this end, Lau et al, (46) transfected muscles cells with the FasL gene and co-transplanted them with islets beneath the kidney capsule and achieved local immunoprotection for the grafted islet, albeit for only 80 days. In a letter to Science, D Green declared this a stunning advance and declared that "It's almost the Holy Grail of immunosuppression to restrict the suppression to the environment of the graft" (47). Selawry and Cameron (35) achieved the same results with long-term imnmunoprotection of the grafted islets and long-term maintenance of normoglycemia in the diabetic rat by co-transplanting the islets with the natural producer of FasL, Sertoli cells. The salient features of terminally differentiated Sertoli cells that make them important and preferable as a transplantation facilitator are 1) they live for the life of the donor and may survive for the life of the recipient host (providing, thereby, long-term FAS-L induced local immunoprotection for the transplanted tissue or cells), 2) they do not divide and 3) they are easily isolated.

Since Sertoli cells secrete many growth enhancing factors including insulin-like growth factor I (55), the presence of Sertoli cells, in addition to their immunoprotective protective properties, may provide additional tropic and growth support to the transplant. Recently, Selawry et al, (48) showed that when cryopreserved pig Sertoli cells were thawed and immediately place in culture with Sertoli cells, there was a significant enhancement of post-thaw survival and insulin secretion when compared to thawed islets not co-cultured with Sertoli cells. They suggested that insulin-like growth factor I may have provided growth factor support to the cell membrane known to be damaged during freezing. Recently Sanberg et al (49–51) demonstrated that Sertoli cells can survive in the brain and, in fact, protect bovine adrenal chromaffin cell xenografts from rejection when co-transplanted into the striatum of the Parkinson's disease rat model. Even more significant, Sertoli cells alone transplanted into the PD rat result in the amelioration of motion dysfunction to the same degree as do chromaffin cells indicating a type of successful growth factor therapy, as yet unknown, provided for by the transplanted Sertoli cells (52). Similar to islet cells, Carneron et al (53) have shown that the post-thaw viability of fetal brain cells is significantly enhanced if the neuron are co-cultured with Sertoli cells again indicating the generalized ability of Sertoli cell secretory products to support the viability of isolated cells. For both islets and neurons, the growth and viability enhancing characteristics of Sertoli cells were evident only when the Sertoli cells were present as opposed to only media soluble factors found in expended pre-conditioned Sertoli cell media.

The extra-testicular utilization of Sertoli cells in facilitated transplantation holds enormous potential based of the cell's ability to provide for long-term localized immunosuppression and generalized growth enhancement of the transplanted cells and tissues. There is a distinct advantage to utilizing whole Sertoli cells rather than specific growth or immunosuppressant factors in that the Sertoli cell appears to continue expressing its desirable transplantation facilitation properties as long as the cell survives in the host, which may be for the life of the recipient. Because Sertoli cells cease mitotic activity following differentiation (54) and do not appear to re-acquire it following transplantation, it may be possible to transplant a stable population of Sertoli cells which remains stable for the life of the host. It is not an understatement to recognize that the utilization of extra-testicular Sertoli cells as transplantation facilitators opens the window to new and potentially significant protocols for transplantation success and represents the beginning "of a new era in transplantation" therapy (47).

In general, systematic. immunosuppression is necessary if successful transplantation is to be achieved in humans. Immunosuppression of the entire body (i e. systemic) can result, eventually, in graft acceptance. It is acquired, however, by placing the individual at medical risk making the immunosuppressant therapy itself more of a liability than a benefit in some cases. For a lack of a better immnosuppressant treatment, systemic immunosuppressants, with Cyclosporine-A (CsA) as the treatment choice, have been used as adjunctive therapy in neural transplantation protocols (Sanberg et al., 1994; Freeman et al., 1994; Borlongan et al., 1995). Arguably, systemic CsA treatment may be contraproductive to successful graft acceptance in the CNS because of its systemic effect and because CsA itself has been shown to cause detrimental side effects and may in fact, be cytotoxic to neural tissues (Berden et al., 1985; deGroen et al., 1984).

It would be useful to develop a mechanism that enhances the productive cell transplantation techniques already utilized for neurodegenerative disorders, such as Parkinson's disease. This mechanism should improve these protocols in ways which would more effectively slow the neurodegenerative disease process, more actively promote the reestablishment of normal neural tissue physiology and better alleviate the functional disabilities associated with the neural tissue dysfunction. Likewise, it would be useful to provide trophic support for the transplanted cells. Further, it would useful if this support lead to the reduction or elimination of systemic immunosuppression while maintaining the ability to immunosuppress locally (i.e. at the graft site) by an immunosuppressant which is biologically tolerated by the host. Sertoli cells may provide this desired option since it is clear from the diabetic studies, as summarized above, that co-transplantation with Sertoli cells will deliver local immunosuppression and promote, therefore, efficient graft acceptance and functional restoration of the tissue-related dysfunction.

SUMMARY OF THE INVENTION

According to the present invention, there is provided a biological chamber including outer walls of Sertoli cells and an inner lumen. Also provided is a transplantation facilitator including a biochamber which is formed from an engineered Sertoli tissue construct. A method of making biochambers by co-culturing facilitator cells and therapeutic cells is also provided. Additionally, there is provided a method of transplanting cells by incorporating therapeutic cells into a biochamber and transplanting the biochamber containing the therapeutic cells. Further, a method of treatment using these engineered biochambers is also included.

DESCRIPTION OF THE DRAWINGS

Other advantages of the present invention will be readily appreciated as the same becomes better understood by reference to the following detailed description when considered in connection with the accompanying drawings wherein:

As shown in FIG. 1B, apical secretion in a closed compartment creates a fluid-filled lumen by appreciating hydrostatic pressure;

As shown in FIG. 2A apical secretion in a closed compartment creates a fluid-filled lumen by appreciating hydrostatic pressure. As shown in FIG. 2B, microgravity coculture results in the integration of therapeutic cells into Sertoli cell biochambers;

DETAILED DESCRIPTION OF THE INVENTION

Generally, the present invention provides a biological chamber system which is used for transplating cells. More specifically, the biochamber is formed of facilitator cells such as, but not limited to, Sertoli cells which form a chamber or vessel having an inner cavity or lumen containing therein a population of cells different than the facilitator cells. In the preferred embodiment, this population of cells include therapeutic cells.

By "Biochamber" or "vessel", it is meant that a number of cells are engineered in such a manner as to form discrete walls about a lumen or center chamber. More specifically, the biochamber is formed by a structural modification of the Sertoli cells, this new structure being similar to the original Sertoli cell structure prior to cell harvesting. It is during this harvesting that the Sertoli cells are reorganized to form a central lumen in which the therapeutic cells are housed within a newly formed micro-environment. This micro environment can contain therein therapeutic cells, which are used for transplantation. By "facilitator cell", as used herein, it is meant to include a cell which is able to provide localized immunosuppression or otherwise facilitate or make more effective the transplant. The facilitator cells provide bio-protection for the therapeutic or transplanted cells. This bio-protection includes, but is not limited to, protection from a biological source such as an immune response, whether cellular or humoral. In the preferred embodiment, the facilitator cell is a Sertoli cell. Such cells, as described hereinbelow, are able to reorganize to form walls defining an inner lumen. The biological/living walls provide a physical as well as an immunological barrier for the cells contained therein. The apical secretions of Sertoli cells contribute to the unique trophic-bridge micro-environment of the luminal spaces in which therapeutic cells reside.

The term "therapeutic cell" as used herein, is meant to include the cells to be transplanted. For example, these therapeutic cells can include, but are not limited to, the following cells: dopaminergic cells, pancreatic islet cells, bovine chromaffin cells and immortalized neuron-like NT2 cells. The cells are therapeutic in that they can secrete hormones, factors, or the like that can have a therapeutic effect upon the host. They, like the Sertoli cell walls, are biosensitive in that they can respond to factors in their environment.

By modifying the harvested Sertoli cell by the methods of the instant invention that the cells reorganize into a tissue structure similar to that observed in the testis. They become a protective and nurturing barrier tissue, encapsulating the therapeutic cells in a unique micro-environment. Because the engineered Sertoli tissue construct captures the therapeutic cells in their new environment, this produces a dynamic support system for the therapeutic cells whereby the discreet units become efficient and viable within this special structure. Each biochamber becomes a discreet transplant unit, both nurtured and immunoprotected, by the surrounding engineered Sertoli tissue.

In the preferred embodiment, Sertoli cells are isolated from a mammal, such as, but not limited to a prepubertal rat or pig testes and co-cultured with a therapeutic cell type in a culture environment that enhances tissue formation. This can be accomplished by co-culturing the different cell types in simulated microgravity culture utilizing the HARV bioreactor or other culture technologies. In a further embodiment, the co-culturing is performed without the microgravity environment.

The addition of a basement membrane-like extracellular matrix to the incubation medium induces the epithelization and polarization of Sertoli cells, and subsequent formation of Sertoli-Sertoli junctional complexes between adjacent Sertoli cells, and the formation of a lumen or lumina. There is segregation of the Sertoli cells away from the therapeutic cells during the process of Sertoli cell epithelization leaving the therapeutic cells residing within the newly-formed luminal spaces. The luminal space(s) islare created during this reorganization of the Sertoli cells and the formation of the Sertoli-Sertoli junctions. These junctions form an intraepithelial barrier similar to that observed in the testis and referred to as the blood-testis barrier. Apical polarization of Sertoli cell secretion is the likely mechanism by which the lumen is formed (FIGS. 1–3) The reorganized Sertoli cells illustrated in FIGS. 1–3 create an item which is referred to as the Sertoli cell biochamber.

The Sertoli cell portion of the biochamber acts as a facilitator or a bridge cell for the transfer of material into and out of the lumen.

Examples of such biochambers, include but are not limited to, Islet, filled Sertoli cell biochambers (SICAs) and NT2 cell-filled biochambers (SNACS) which exemplify how therapeutic cell types can be incorporated into the Settoli cell biochamber. SICAs secrete insulin in response to a glucose challenge (180 mg %) and also suppress activated lymphocytic proliferation (16). Similarly, SNACs enhance the differentiation of NT2 cells to the dopaminergic phenotype (17–18) and likewise provide for immunoprotection of the neurons as judged by the expression of FasL on the Sertoli cells (see FIG. 3). SICAs and SNACs are therapeutic cell-filled Sertoli cell biochamber products created by this tissue engineering protocol and are designed for the use in therapeutic transplantation treatments for serious diseases such as diabetes and Parkinson's disease Since Sertoli cells are terminally differentiated, and the cells are mitotically inactive. They live for a long period of time, and potentially as long as any therapeutic cell type that can be engineered into the Sertoli cell biochamber. If transplanted in a Sertoli cell biochamber, therapeutic cells can be protected against immune surveillance and subsequent rejection in a micro-environment (provided for by Sertoli cell secreted growth and trophic factors) that also maintains and stimulates theirfunctional phenotypes on a lona-term basis. This has a significant impact on the successful transplantation treatment of many serious diseases and on the status of transplantation biology in general.

The above discussion provides a factual basis for the use of Sertoli cell biochambers. The methods used with and the utility of the present invention can be shown by the following non-limiting examples and accompanying figures.

EXAMPLES

General Methods

General methods in molecular biology: Standard molecular biology techniques known in the art and not specifically described were generally followed as in Sambrook et al., *Molecular Cloning: A Laboratory Manual,* Cold Spring Harbor Laboratory Press, New York (1989), and in Ausubel et al., *Current Protocols in Molecular Biology,* John Wiley and Sons, Baltimore, Maryland (1989) and in Perbal,: *A Practical Guide to Molecular Cloning,* John Wiley & Sons, New York (1988), and in Watson et al., *Recombinant DNA,* Scientific American Books, New York and in Birren et al (eds) *Genome Analysis: A Laboratory Manual Series,* Vols. 1–4 Cold Spring Harbor Laboratory Press, New York (1998) and methodology as set forth in U.S. Pat. Nos. 4,666,828; 4,683,202; 4,801,531; 5,192,659 and 5,272,057 and incorporated herein by reference. Polymerase chain reaction (PCR) was carried out generally as in PCR Protocols: A Guide To Methods And Applications, Academic Press, San Diego, Calif. (1990). In-situ (In-cell) PCR in combination with Flow Cytometry can be used for detection of cells containing specific DNA and mRNA sequences (Testoni et al, 1996, Blood 87:3822.)

General methods in immunology: Standard methods in immunology known in the art and not specifically described are generally followed as in Stites et al.(eds), Basic and Clinical Immunology (8th Edition), Appleton & Lange, Norwalk, Conn. (1994) and Mishell and Shuigi (eds), Selected Methods in Cellular Immunology, W. H. Freeman and Co., New York (1980).

Immunoassays

In general, immunocytochemistry ELISAs are the preferred immunoassays employed to assess a specimen. These assays are well known to those skilled in the art. Both polyclonal and monoclonal antibodies can be used in the assays. Where appropriate other immunoassays, such as radioimrnunoassays (RIA) can be used as are known to those in the art. Available immunoassays are extensively described in the patent and scientific literature. See, for example, U.S. Pat. Nos. 3,791,932; 3,839,153; 3,850.752. 3,850,578; 3,853,987; 3,867,517; 3,879,262; 3,901,654; 3,935.074; 3,984,533; 3,996,345; 4,034,074; 4,098,876; 4,879,219; 5,011,771 and 5,281,521 as well as Sambrook et al, *Molecular Cloning: A Laboratory Manual,* Cold Springs Harbor, New York, 1989

Delivery of Gene Products/Therapeutics (Compound)

The compound of the present invention is administered and dosed in accordance with good medical practice, taking into account the clinical condition of the individual patient, the site and method of administration, scheduling of administration, patient age, sex, body weight and other factors known to medical practitioners. The pharmaceutically "effective amount" for purposes herein is thus determined by such considerations as are known in the art. The amount must be effective to achieve improvement including but not limited to improved survival rate or more rapid recovery, or improvement or elimination of symptoms and other indicators as are selected as appropriate measures by those skilled in the art.

The biochambers of the instant invention can be administered in various ways. These include subcutaneously or parentally, including intravenous, intraarterial, intramuscular, intraperitoneal and intranasal administration. Pharmaceutically acceptable carriers, diluents, adjuvants and vehicles are also useful for administration of the biochambers. These refer to any diluent, carrier, adjuvant or vehicle as commonly, known to one of ordinary skill in the art.

Example 1

Recently, Sertoli cells have been utilized to facilitate islet transplantation on the basis that the testis-derived cells provide localized immunoprotection at the graft site and stimulate islet viability. The relationship between Sertoli cells and β-cells is not yet well defined in vivo nor in vitro. To further evaluated this relationship and to promote Sertoli/islet cell 3-dimensional aggregation (SICA) in vitro, Sertoli cells and islets were co-cultured in simulated microgravity using the NASA high aspect rotation velocity (HARV) bioreactor.

Sertoli cells, harvested from mammals by methods as known by those of skill in the art, and islets, obtained by methods known to those of skill in the art as in Korbutt et al, were isolated from neonatal pigs by routine enzymatic digestion. Sertoli cells were. placed immediately into HARVs at the time of isolation. Isolated islets were precultured in flasks for 14 days (to expedite the removal of exocrine tissue) prior to incubation in HARV's with or without Sertoli cells. HARV co-cultures were incubated at 37° for 28 days in defined incubation medium consisting of DMEM; F-12 supplemented with ITS+Retinol, and 1% Matrigel. Every 48 hours, 4 ml of media was removed and replaced wtit fresh media. The SICAs were exposed to a standard glucose challenge (180 mg % glucose) after which samples were collected every ten minutes for an hour and subsequently assayed for insulin by radioimmunoassay. Cell viability was determined by trypan blue exclusion, the presence of β-cells was determined by differential staining with dipherrylthiocarbazone and/or insulin immunostaining, and Sertoli cells were determined by FAS-L immunostaining.

By the end of the incubation period, Sertoli cells and islets had formed sizable (3–10 mm diameter) tissue constructs, with those formed in Matrigel mediums being larger. Cell viability was high (>80%) and β-cells were detected in both SICAs In the three separate HARV incubations, the presence of Sertoli cells in SICA's enhanced the basal and total amount of insulin secreted in response to the glucose challenge when compared to islet-only HARV monocultures. In the presence of Sertoli cells, the SICA's insulin response to the elevated glucose was quicker and appeared to be prolonged.

Example 2

Figure 6:
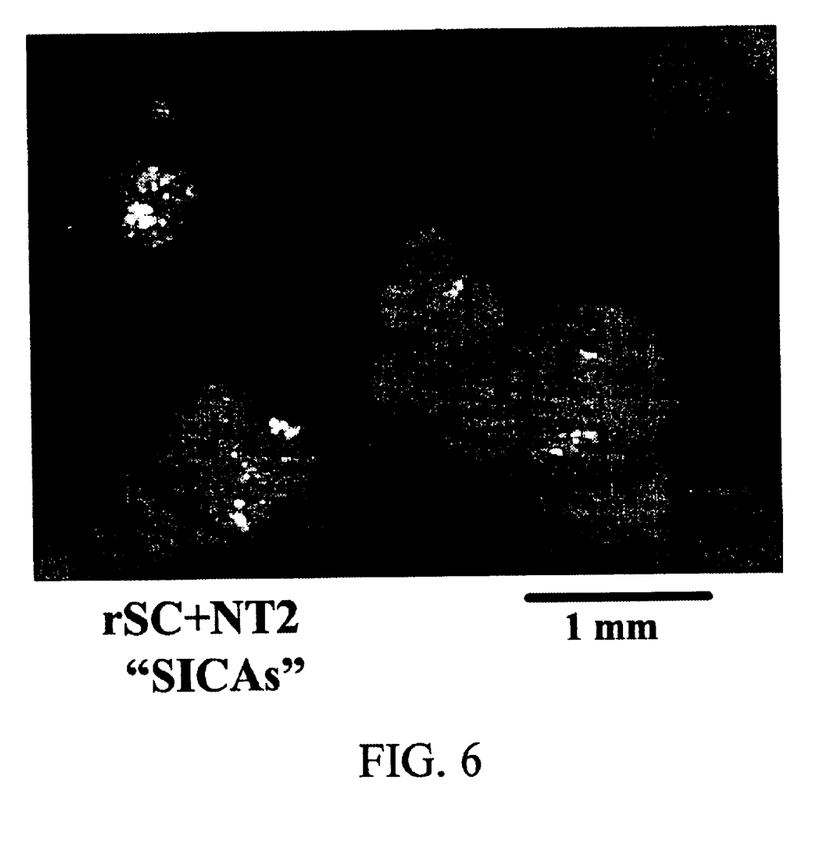
FIG. 6 is a photograph of Sertoli-Neuron-Aggregate-Cells (SNACS for in vitro following co-culture of rat Sertoli cells and NT2 neuros in simulated microgravity utilizing the High Aspect Rotation Velocity (HARV) bioreactor and 1 week HARV co-culture)

Formation of Sertoli-neuron Aggregated Cells(SNACs) by Simulated Microgravity Coculture of Sertoli Cells and Imortalized NT2 Cells Sertoli cells also have been utilized to facilitate the transplantation of dopaminergic cells into the brain as a treatment protocol for Parkinson's since Sertoli cells appear to provide localized immunoprotection at the graft site and to stimulate nerve cell viability: (Sanberg, P. R., C. V. Borlongan, A. I. Othberg, S. Saporta, T. B. Freeman and D. F. Cameron. Testis-derived Sertoli cells have a trophic effect on dopamine neurons and alleviate hemiparkinsonism in rats. Mature medicine, 3(10):1129–1132.). To enhance this transplantation treatment protocol, as was utilized in the diabetes transplantation (see Example 1). Sertoli cells and the immortalized NT2 cell line were cocultured in simulated MICROGRAVITY using the NASA high aspect rotation velocity (HARV) bioreactor. Sertoli cells were isolated from peripuberital rats and placed immediately in HARVs along with the NT2 cells. Maintenance medium was DMEM/F12 supplemented with ITS+ and retinal and ±1% Matrigel (MG). Cocultures were incubated at 37° C. for one or two weeks in maintenance medium which was replaced when needed or every 48 hours. As with Senoli cells and islets, cells organized to form Sertoli-neuron-aggregated cells (SNACs) (FIG. 6).

At the time of SNACs collection, cell viability was determined by trypan blue exclusion SNACs were processed for morphological analysis with 3% gluteraldehyde and processed into Epon/Araldite or fixed with 4% paraformaldehyde and processed into OCT for cryosectioning. Cryosections were immunostained for FasL (Sertoli cell marker), NuMa (NT2 cell marker) and tyrosine hydroxylase (TH-enzyme marker for dopamine synthesis).

Following the incubation period, cell viability was high (>90%) and there was segregation of Sertoli cells (peripherally distributed) and NT2 cells (centrally distributed) when, incubated with MG. Positive FasL immunostaining was localized peripherally consistent with Sertoli cell distribution whereas NuMa localization was consistent with the distribution of NT2 cells. Some centrally located cells showed positive immunostaining for TH. It appeared that with MG, the Sertoli biochamber tissue construct was achieved with these two cell types, as described for the SICA (see Example 1). It is therefore concluded that the HARV coculture of Sertoli cells, and NT2 neurons with MG, resulted in the formation of NT2-filled Sertoli biochambers comprised of FasL positive Sertoli cells forming the biochamber wall and NuMa positive NT2 cells residing within the biochamber. The expression of TH suggests that some of the NT2 cells had differentiated into the dopaminergic phenotype indicating the use of these SNACs transplantation protocols for the treatment of experimental Parkinson's disease.

Example 3

Figure 4:
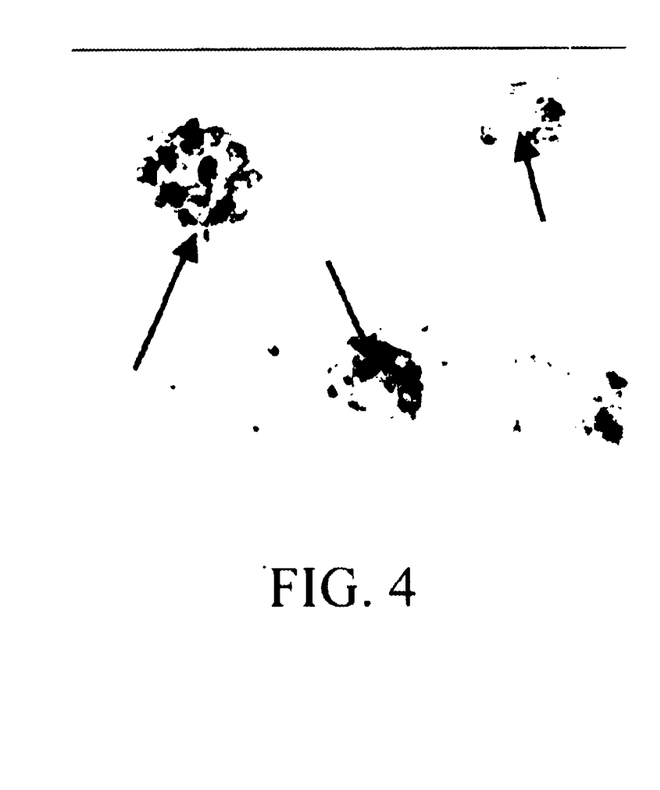
FIG. 4 is a photograph showing Sertoli cells (SC) and islets (arrows) in a Sertoli-islet tissue construct created in a conventional co-culture; B-cells are immunostained for insulin.
Figure 5:
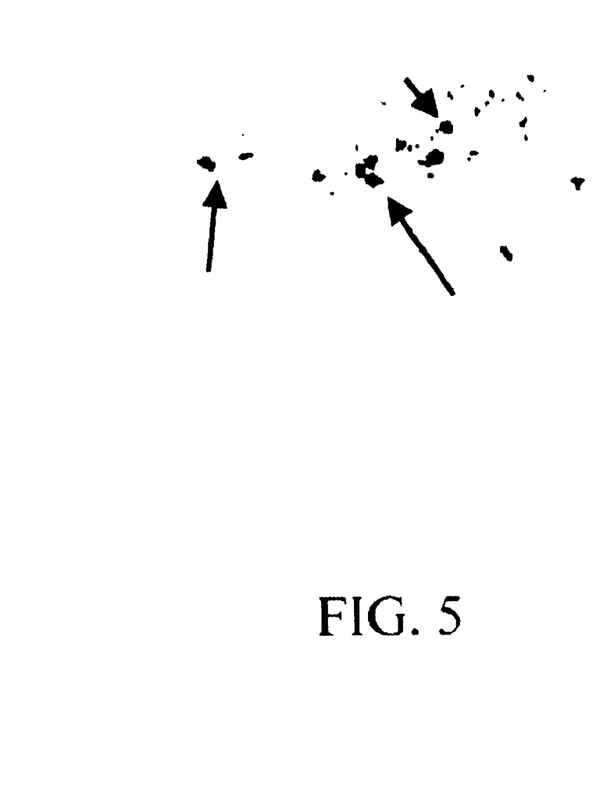
FIG. 5 is a photograph of Sertoli cells (SC) and B-cells (arrows) in a Sertoli-islet tissue construct created in a conventional co-culture, B-cells are immunostained for insulin.

Isolated Sertoli cells from peripubertal rats and pancreatic islets from neonatal pigs were co-cultured by conventional culture technology in the same medium described for the HARV simulated microgravity coculture. Sertoli cells were pre-plated 48 hours on plastic or Matrigel substrates. Pre-treated isolated pig islets were added to the Sertoli cell-enriched monoculture 24 hours later. This Sertoli-Islet co-culture was incubated at 37° C. and within 24 hr. islets had attached to and integrated into the underlying Sertoli cells. Within another 48–72 hrs, Sertoli cells reorganized into spherical or chord-like aggregates. This process was enhanced for those co-cultures in which Sertoli cells had been plated on the Matrigel. Islets appeared to retain their structural integrity better iin the non-Matrigel co-cultures (FIG. 4) than in the cocultures not having a Matrigel substrate (FIG. 5). Tissue constructs of Sertoli cells and pancreatic islet cells can be created in conventional coculture in a similar manner as that observed in simulated microgravity coculture Throughout this application, various publications, including United States patents, are referenced by author and year and patents by number. Full citations for the publications are listed below. The disclosures of these publications and patents in their entireties are hereby incorporated by reference into this application in order to more fully describe the state of the art to which this invention pertains.

The invention has been described in an illustrative manner, and it is to be understood that the terminogoly which has been used is intended to be in the nature of words of description rather than of limitation.

Obviously, many modifications and variations of the present invention are possible in light of the above teachings. It is, therefore, to be understood that within the scope of the appended claims, the invention may be practiced otherwise than as specifically described.

References

1. Kaufman, et al. (1990).
2. Evans, et al. (1990).
3. Horaguchi, et al. (1981).
4. Kneteman, et al. (1990).
5. Ricordi, et al. (1990).
6. Thomnpson et al. (1990).
7. Calafiore, et al. (1990).
8. Gray, et al. (1984).
9. Scharp, et al. (1987).
10. Alderson, et al. (1987).
11. Ricordi, et al. (1989).
12. Scharp, D. W. (1988).
13. Kneteman, et al. (1986).
14. Warmock, et al. (1988).
15. Warnock, et al. (1989).
16. Kuhn, et al. (1985).
17. Naji, et al. (1981).
18. Weringer, et al. (1985).
19. Prowse, et al. (1986).
20. Selawry (1985).
21. Selawry et al. (1987).
22. Selawry, et al. (1986).
23. Whitmore, et al. (1978).
24. Head, et al. (1983).
25. Head, et al. (1983).
26. Hedger, M. P (1989).
27. Barker et al. (1968).
28. Selawry, et al. (1989).
29. Martin, D C. (1982).
30. Cameron, et al. (1990).
31. Fawcett. et al. (1973).
32. Born, et al. (1982).
33. Born, et al. (1981).
34. Williams et al (1978)
35. Selawry, et al. (1993).
36. Bardin, et al. (1988).
37. Griswold, M. D. (1993).
38. Selawry. et al. (1991).
39. DeCesarts, et al. (1992).
40. Cantrell, et al. (1984).
41. Leapman, et al. (1981).
42. Hess, A D. (1985).
43, Green, et al. (1978).
44. Homan, et al. (1980).
45. Beltgrau et al (1995)
46. Lau, et al. (1996).
47. Wickelgren, L. (1996).
48. Selawry, et al. (1996).
49. Sanberg, et al. (1995).
50. Sanberg, et al. (1966).
51. Sanberg, et al. (1996).
52. Borlongan, et al. (1996).
53. Cameron et al. (1996).
54. Gondos. et al. (1993).
55. Skinner, et al. (1993).
56. Edgington, S. M. (1992).
57. Goodwin, et al. (1993).
58. Goodwin, et al. (1993).
59. Goodwin, et al. (1992).
60. Becker et al. (1993).
67. Cameron et al. (1991).
68. Cameron, et al. (1993).
69. London, etal (199).
70. Cameron et al. (1990).
71. Schwarz, et al. (1992).
72. Goodwin, et al. (1996).
73. Suda, et al. (1993).
74. Towbin, et al. (1979).
75. Prewett, et al. (1993).
76. Goodwin, et al. 91993).
77. Goodwin, et al. (1993).

What is claimed is:

1. A biochamber comprising a lumen, an outer wall defining said lumen, and a plurality of non-Sertoli cells contained within said lumen, wherein said outer wall comprises Sertoli cells, and wherein said plurality of non-sertoli cells are selected from the group consisting of neuronal cells, NT2 cells, pancreatic islet cells, dopaminergic cells, and bovine chromaffin cells.

2. The biochamber according the claim 1, wherein junctional complexes are formed between adjacent Sertoli cells of said outer wall.

3. The biochamber according to claim 1, wherein said Sertoli cells are arranged as a monolayer.

4. The biochamber according to claim 1, wherein said plurality of non-Sertoli cells comprises pancreatic islet cells.

5. The biochamber according to claim 1, wherein said plurality of non-Sertoli cells comprises neuronal cells.

6. The biochamber according to claim 5, wherein said neuronal cells are NT2 neurons.

7. The biochamber according to claim 1, wherein said Sertoli cells of said outer wall provide immunoprotection to said pluralily of non-Sertoli cells within said lumen upon transplantation of said biochamber.

8. The biochamber according to claim 1, wherein said biochamber is spherical in shape.

9. A biochamber comprising a lumen, an outer wall, and a plurality of non-Sertoli cells contained within said lumen, wherein said outer wall monolayer of Sertoli cells that define said lumen, whrein said monolayer of Sertoli cells encapsulate said plurality of non-Sertoli cells, wherein junctional complexes are formed between adjacent Sertoli cells of said outer wall, and wherein said plurality of non-Sertoli cells are selected from the group consisiting of neuronal cells, NT2 cells, pancreatic islet cells, dopaminergic cells, and bovine chromaffin cells.

10. A method of making a biochamber comprising:
co-culturing Sertoli cells and non-Sertoli cells in the presence of a basement membrane preparation for a period of time sufficient for the Sertoli cells to form an outer wall that encapsulates a plurality of the non-Sertoli cells, wherein the non-Sertoli cells are selected from the group consisting of neuronal cells, NT2 cells, pancreatic islet cells, dopaminergic cells and bovine chromaffin cells.

11. The method accordinig to claim 10, wherein said co-culturing is carricd out under microgravity conditions.

12. The method according to claim 10, wherein the basement membrane preparation causes epithelization and polarization of the Sertoli cells, thereby inducing the Sertoli cells to form the outer wall that encapsulates the plurality of non-Sertoli cells.

13. The method according to claim 10, wherein the basement membrane preparation comprises MATRIGEL.

14. The method according to claim 10, wherein junctional complexes are formed between, adjacent Sertoli cells of said outer wall.

15. The method of claim 10, wherein the outer wall comprises a monolayer of Sertoli cells.

16. A method of transplating cells comprising the steps of transplanting a biochamber into a host, wherein the biochamber comprises a lumen, an outer wall defining said lumen, and a plurality of non-Sertoli cells containedj within said lumen, wherein said outer wall comrpises Sertoli cells, and wherein the non-Sertoli cells are selected from the group consisting of neuronal cells, NT2 cells, pancreatic islet cells, dopaminergic cells, and bovine chromaffin cells.

17. The method according to claim 16, wherein the outer wall comprises a monolayer of Sertoli cells.

18. The method according to claim 16, wherein the non-Sertoli cells are secreting cells.

19. The method according to claim 16, wherein junctional complexes are formed between adjacent Sertoli cells of said outer wall.

20. The method of claim 16, wherein said method further comprises making a biochamber prior to said transplanting, wherein said makings comprises co-culturing the Sertoli cells and non-Sertoli cells in the presence of a basement membrane preparation for a period of time sufficicnt for the basement membrane preparation to induce the Sertoli cells to form an outer wall that encapsulates the plurality of non-Sertoli cells within the lumen.

21. The method of claim 20, wherein the basement membrane preparation comprises MATRIGEL.

22. The method of claim 20, wherein the co-culturing is carried out under microgravity conditions.

23. The method of claim 22, wherein the basement membrane preparation comprises MATRIGEL.

24. A method of making a biochamber comprising co-culturing Sertoli cells and non-Sertoli cells under microgravity conditions for a period of time sufficient for the Sertoli cells to form an outer wall that encapsulates a plurality of the non-Sertoli cells, wherein said co-culturing is carried out in culture medium containing a basement membrane preparation, and wherein the non-Sertoli cells are selected from the group consisting of neuronal cells, NT2 cells, pancreatic islet cells, dopaminergic cells, and bovine chromaffin cells.

25. The method of claim 24, wherein the basement membrane preparation comprises MATRIGEL.

* * * * *

UNITED STATES PATENT AND TRADEMARK OFFICE
CERTIFICATE OF CORRECTION

PATENT NO. : 6,790,441 B1
DATED : September 14, 2004
INVENTOR(S) : Don F. Cameron et al.

It is certified that error appears in the above-identified patent and that said Letters Patent is hereby corrected as shown below:

Title page,
Item [57], ABSTRACT,
Line 6, "facilitator celes" should read -- facilitator cells --.

Column 1,
Line 9, "inventions" should read -- invention --.
Line 18, "prefened" should read -- preferred --.
Line 19, "the. administration" should read -- the administration --.
Line 25, "neurodegenetative" should read -- neurodegenerative --.
Line 27, "Lindvall et al," should read -- Lindvall et al., --.
Line 28, "Freeman et al," should read -- Freeman et al., --
Line 33, "Wictorin et al," should read -- Wictorin et al. --
Line 38, "Sanberg et, al 1994" should read -- Sanberg et al., 1994 --.
Line 38, "viabie" should read -- viable --.
Line 39, "inclcude" should read -- include --.
Line 61, "immunosuppfessicn" should read -- immunosuppression --.

Column 2,
Line 2, "(MHC) In the" should read -- (MHC) in the --
Line 5, "diabeiic" should read -- diabetic --.
Line 6, "MHC-incompatibie" should read -- MHC-incompatible --.
Line 17, "non-imminosuppressed" should read -- non-immunosuppressed --.
Line 56, "Wekerie" should read -- Wekerle --.
Line 62, "in to" should read -- into --.

Column 3,
Line 8, "involvedeither" should read -- involved either --.
Line 9, "eliminatin" should read -- eliminating --.
Line 10, "Sewiary" should read -- Selawry --.
Line 17, "Serioli" should read -- Sertoli --.
Line 34, "secret" should read -- secrete --.
Line 39, "proteins. some of" should read -- proteins, some of --.
Line 46, "occurrinry" should read -- occurring --.
Line 57, "(39) It" should read -- (39). It --.
Line 59, "receptors,. while" should read -- receptors, while --.

Column 4,
Line 6, "ppealing" should read -- appealing --.
Line 7, "Beligrau" should read -- Bellgrau --.
Line 10, "gid" should read -- gld --.

UNITED STATES PATENT AND TRADEMARK OFFICE
CERTIFICATE OF CORRECTION

PATENT NO. : 6,790,441 B1
DATED : September 14, 2004
INVENTOR(S) : Don F. Cameron et al.

It is certified that error appears in the above-identified patent and that said Letters Patent is hereby corrected as shown below:

Column 4 (cont'd),
Line 13, "Pypress" should read -- express --.
Line 15, "g/d" should read -- gld --.
Line 21, "subjacent the kidney" should read -- subjacent to the kidney --.
Line 25, "Cyclosporin A" should read -- Cyclosporine A --.
Line 30, "muscles cells" should read -- muscle cells --.
Line 45, "FAS-L" should read -- FasL --.
Line 51, "tropic" should read -- trophic --.
Line 53, "pig Sertoli cells" should read -- pig islet cells --.
Line 54, "place in culture" should read -- placed in culture --.

Column 5,
Line 2, "Carneron" should read -- Cameron --.
Lines 57-58, "it would useful" should read -- it would be useful --.

Figure 7A:
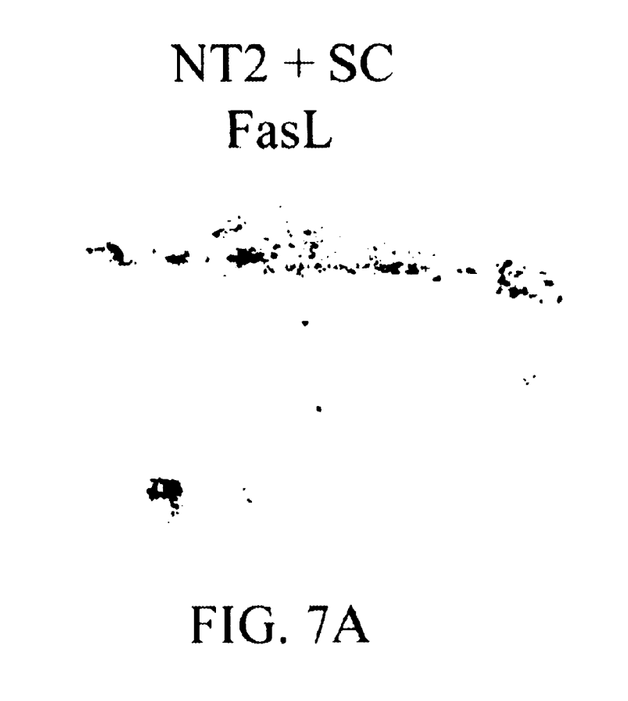
FIGS. 7A and 7B is a photograph of immunocytochemical staining of mouse FasL, and human nuclear matrix proteins in Sertoli-Neuron Aggregated Cells (SNACS) following HARV incubated co-cultures (1 week HARV co-culture).
Figure 7B:
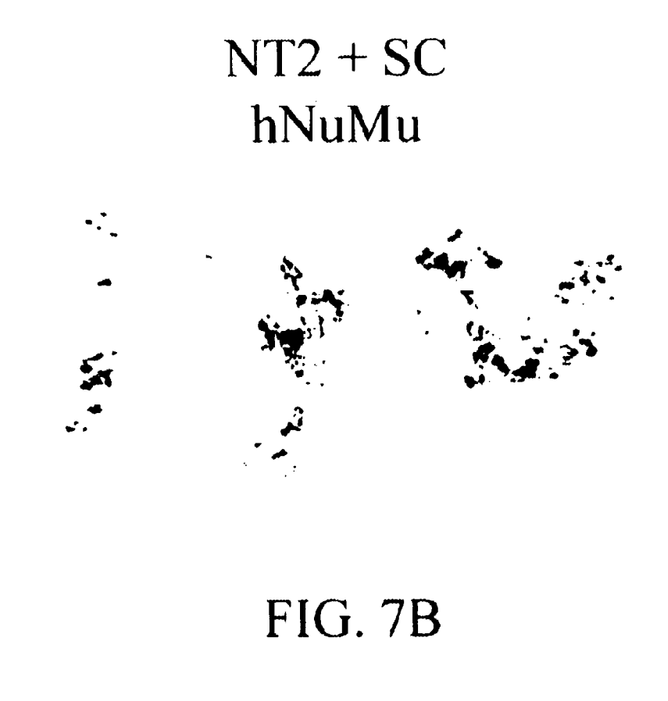

Column 6,
Line 21, "information" should read -- formation --.
Line 30, "coculture" should read -- co-culture --.
Line 34, "immunostatining" should read -- immunostaining --.
Line 36, "Fasl, by Sertoli" should read -- FasL by Sertoli --.
Line 53, "(SNACS for" should read -- (SNACs) for --.
Line 54, "neuros" should read -- neurons --.
Line 55, "bioreactor and 1 week" should read -- bioreactor (1 week --.
Line 57, "FIGS. 7A and 7B is a photograph" should read -- FIGS. 7A and 7B are photographs --.
Line 59, "(SNACS)" should read -- (SNACs) --.
Line 66, "transplating" should read -- transplanting --.

Column 7,
Lines 14-15, "micro environment" should read -- micro-environment --.

Column 8,
Line 4, "islar" should read -- is/are --.
Line 10, "(FIGS. 1-3) The" should read -- (FIGS. 1-3). The --.
Line 17, "Islet, filled" should read -- Islet-filled --.
Line 18, "(SNACS)" should read -- (SNACs) --.
Line 20, "Settoli" should read -- Sertoli --.
Line 30, "disease" should read -- disease. --.
Line 39, "theirfunctional" should read -- their functional --.
Line 39, "lona-term" should read -- long-term --.
Line 56, "Perbal,: A" should read -- Perbal, A --.
Line 59, "Birren et al" should read -- Birren et al. --.

UNITED STATES PATENT AND TRADEMARK OFFICE
CERTIFICATE OF CORRECTION

PATENT NO. : 6,790,441 B1
DATED : September 14, 2004
INVENTOR(S) : Don F. Cameron et al.

It is certified that error appears in the above-identified patent and that said Letters Patent is hereby corrected as shown below:

Column 9,
Line 3, "al," should read -- al., --.
Line 3, "3822.)" should read -- 3822). --.
Line 6, "et al.(eds)" should read -- et al. (eds) --.
Line 8, "Shuigi" should read -- Shiigi --.
Line 17, "radioimrnunoassays" should read -- radioimmunoassays --.
Line 20, "3,850.752." should read -- 3,850,752; --.
Line 22, "3,935.074" should read -- 3,935,074 --.
Lines 23-24, "et al," should read -- et al., --.
Line 25, "1989" should read -- 1989. --.
Line 42, "parentally" should read -- parenterally --.
Line 56, "further evaluated this" should read -- further evaluate this --.
Lines 63-64, "et al," should read -- et al., --.
Line 65, "were. placed" should read -- were placed --.

Column 10,
Line 1, "HARV's" should read -- HARVs --.
Lines 5, 17 and 47 "Matrigel" should read -- MATRIGEL --.
Line 12, "dipherrylthiocarbazone" should read -- diphenylthiocarbazone --.
Line 13, "FAS-L" should read -- FasL --.
Line 19, "SICAs In" should read -- SICAs. In --.
Lines 20 and 23, "SICA's" should read -- SICAs --.
Line 28, "cells(SNACs)" should read -- cells (SNACs) --.
Line 35, "viability: (Sanberg" should read -- viability (Sanberg --.
Line 39, "1132.)." should read -- 1132). --.
Line 45, "peripuberital" should read -- peripubertal --.
Line 50, "Senoli cells" should read -- Sertoli cells --.

Column 11,
Lines 19 and 34, "coculture" should read -- co-culture --.
Lines 20, 28 and 30, "Matrigel" should read -- MATRIGEL --.
Line 29, "iin the" should read -- in the --.
Line 29, "non-Matrigel" should read -- non-MATRIGEL --.
Line 30, "cocultures" should read -- co-cultures --.
Lines 32-33, "coculture" should read -- co-culture --.
Line 43, "terminogoly" should read -- terminology --.

UNITED STATES PATENT AND TRADEMARK OFFICE
CERTIFICATE OF CORRECTION

PATENT NO. : 6,790,441 B1
DATED : September 14, 2004
INVENTOR(S) : Don F. Cameron et al.

It is certified that error appears in the above-identified patent and that said Letters Patent is hereby corrected as shown below:

Column 12,
Line 61, "non-sertoli" should read -- non-Sertoli --.
Line 65, "according the claim" should read -- according to claim --.

Column 13,
Line 17, "wall monolayer" should read -- wall comprises a monolayer --.
Line 35, "carricd" should read -- carried --.
Line 44, "between, adjacent" should read -- between adjacent --.

Column 14,
Line 6, "containedj" should read -- contained --.
Line 20, "makings" should read -- making --.
Line 22, "sufficicnt" should read -- sufficient --.

Signed and Sealed this

Fourteenth Day of June, 2005

JON W. DUDAS
*Director of the United States Patent and Trademark Office*